United States Patent [19]

Taylor

[11] Patent Number: 4,547,153
[45] Date of Patent: Oct. 15, 1985

[54] ORTHODONTIC APPLIANCE

[76] Inventor: Robert F. Taylor, 1528 Oakwood Dr., Memphis, Tenn. 38116

[21] Appl. No.: 681,387

[22] Filed: Dec. 13, 1984

[51] Int. Cl.⁴ .............................................. A61C 3/00
[52] U.S. Cl. ......................................... 433/11; 433/8; 433/18; 433/10
[58] Field of Search ....................... 433/10, 11, 13, 18, 433/19, 21, 8

[56] References Cited

U.S. PATENT DOCUMENTS

| 2,548,864 | 4/1951 | Brusse | 433/11 |
| 3,205,577 | 9/1965 | Linde | 433/10 |
| 3,353,271 | 11/1967 | Blechman | 433/18 |
| 4,103,423 | 8/1978 | Kessel | 433/10 |
| 4,149,314 | 4/1979 | Nonnenmann | 433/13 |
| 4,180,912 | 1/1980 | Kesling | 433/8 |
| 4,355,975 | 10/1982 | Fujita | 433/11 |
| 4,416,627 | 11/1983 | Beazley | 433/8 |
| 4,424,030 | 1/1984 | Smiley et al. | 433/18 |

Primary Examiner—John J. Wilson
Attorney, Agent, or Firm—Walker & McKenzie

[57] ABSTRACT

A plurality of brackets are fixedly mounted to various specific ones of a patient's teeth by adhesive or the like. Each bracket is provided with a slot for receiving an elongated arch wire in such a manner that a corrective force will be exerted against the patient's teeth through the brackets. Further, each bracket is provided with grooves for receiving ridges on auxiliary members to exert additional corrective forces to the teeth. A spring-type clamp or bail is used to hold a cap over the slot and to, in combination with the cap, hold the arch wire to within the slot as well as hold the auxiliaries in place on the bracket.

9 Claims, 23 Drawing Figures

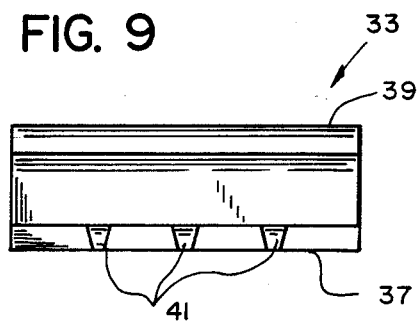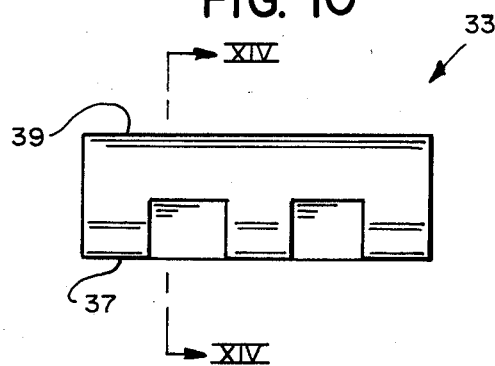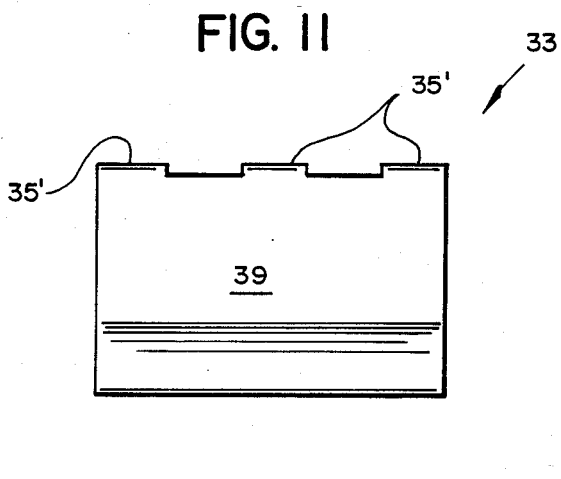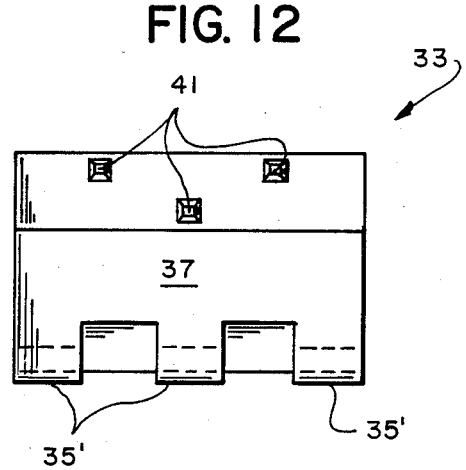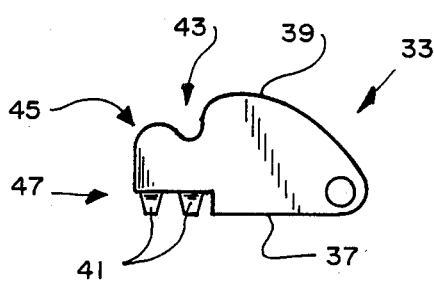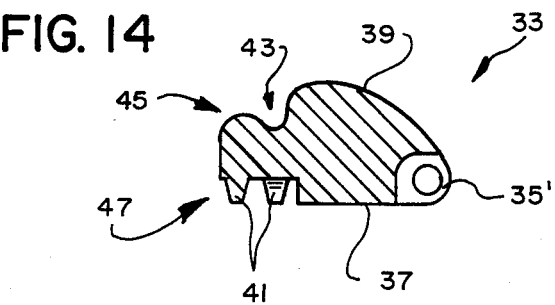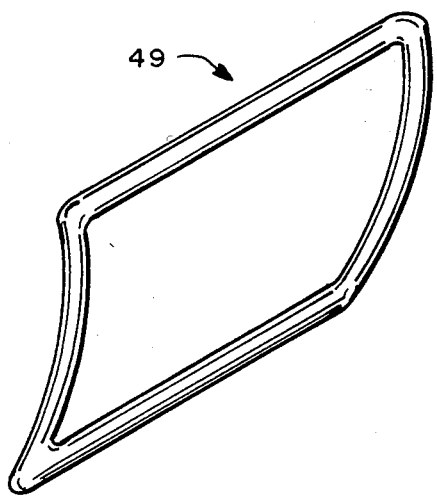

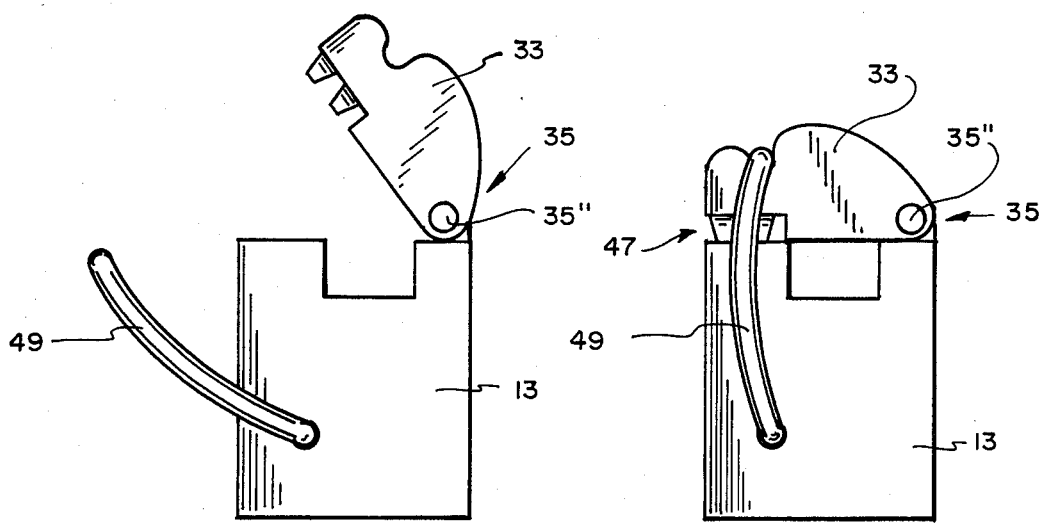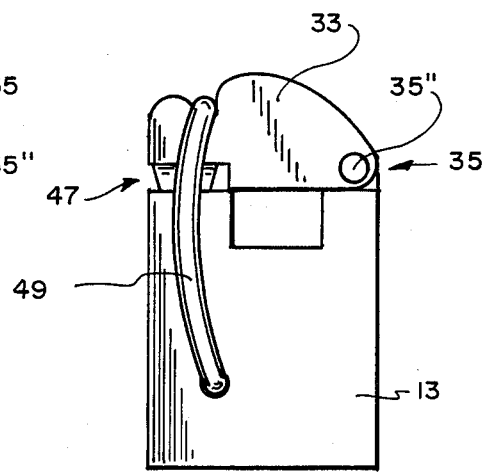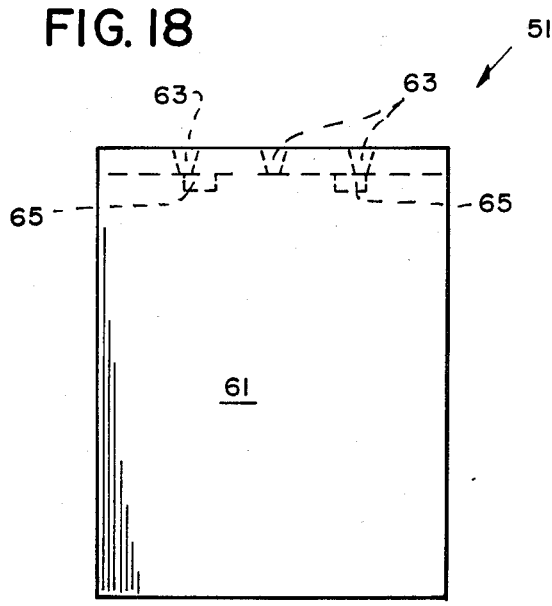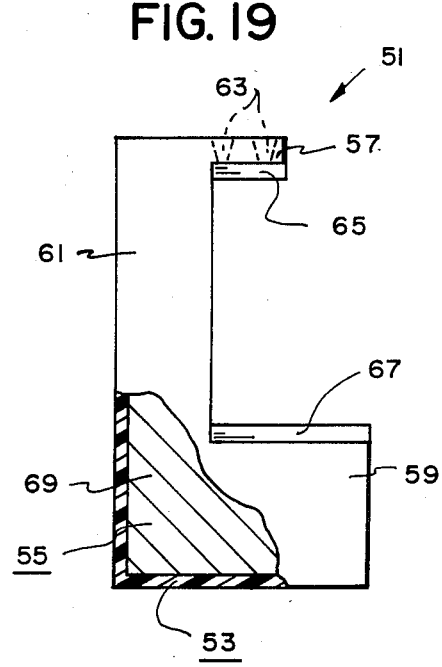

4,547,153

ORTHODONTIC APPLIANCE

BACKGROUND OF THE INVENTION

1. Field of the Invention

The present invention relates, in general, to orthodontic appliances for exerting controlled corrective force against a patient's teeth.

2. Description of the Prior Art

Heretofore, various appliances have been developed for exerting controlled corrective force to a patient's teeth to straighten the patient's teeth and the like. See, for example, Traiger, U.S. Pat. No. 3,092,907; Waldman, U.S. Pat. No. 3,158,934; Blechman, U.S. Pat. No. 3,353,271; Noble, U.S. Pat. No. 3,984,915; Nelson, U.S. Pat. No. 4,017,973; and Smiley, U.S. Pat. No. 4,424,030. None of the above patents disclose or suggest the present invention.

A typical orthodontic appliance employed for the purpose of exerting a corrective force on certain teeth in order to correct the position of the teeth in relation to other teeth commonly includes a plurality of substantially block-like members often referred to as tubes or brackets for being fixedly attached to a patient's teeth in various manners such as by way of adhesive, or the like, and an arch wire for being attached to the brackets to exert a controlled force therethrough. The arch wire may be attached to the brackets in various manners, such as by way of ligatures, to tie the arch wire to the bracket, clamps, detachable screws and the like.

SUMMARY OF THE INVENTION

The present invention is directed toward improving upon prior orthodontic appliances. The concept of the present invention is to provide a self-locking bracket which does not require the arch wire to be attached thereto by ligatures, which permits tension setting of the arch wire in the bracket and which permits alteration of any attachment without the removal of the bracket.

The orthodontic applicance of the present invention comprises, in general, a bracket for being fixedly attached to a patient's teeth, the bracket having a slot for receiving an arch wire; a cap provided over the face of the bracket; and a clamp means for holding the cap against the bracket to coact with the cap to hold the arch wire within the slot.

BRIEF DESCRIPTION OF THE DRAWINGS

FIGS. 9-13 are orthographic views of a cap of the orthodontic appliance of the present invention.

FIG. 14 is a sectional view substantially as taken on line XIV—XIV of FIG. 10.

FIG. 15 is a perspective view of a bail member of the orthodontic appliance of the present invention.

FIG. 16 is an elevational view showing the bracket, cap and bail member coupled to one another with the cap and bail member in opened positions.

FIG. 17 is an elevational view similar to FIG. 16 but with the cap and bail member in closed positions.

FIGS. 18-21 are orthographic views of an auxiliary means of the orthodontic appliance of the present invention with a portion of FIGS. 19 and 20 broken away to more clearly show the structure thereof.

DESCRIPTION OF THE PREFERRED EMBODIMENT

Figure 1:
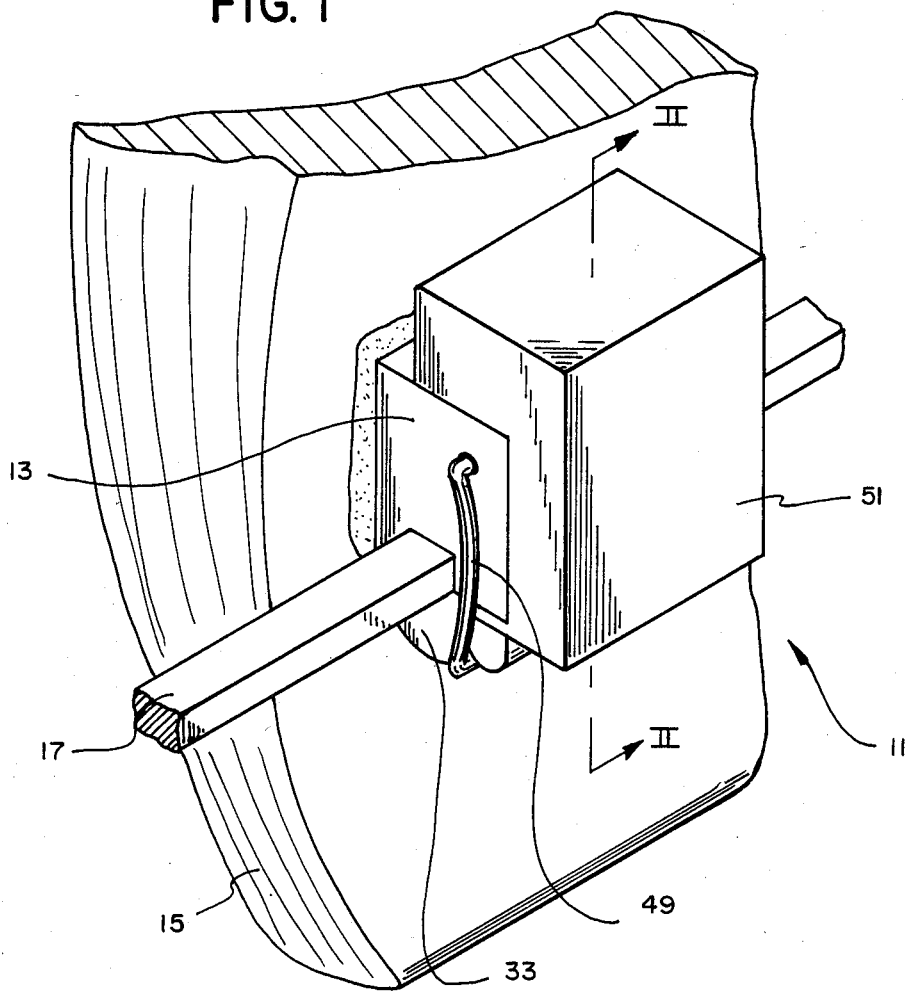
FIG. 1 is a perspective view of the orthodontic appliance of the present invention shown attached to a tooth.

The orthodontic appliance 11 of the present invention is of the type that includes a plurality of brackets 13 for being fixedly attached to various ones of a patient's teeth 15 and an arch wire 17 for being attached to the bracket 13 and for causing a corrective force to be exerted against the patient's teeth 15 through the brackets 13 (see FIGS. 1, 2, 22 and 23).

The arch wire 17 is of any typical construction and preferably has a substantially rectangular cross-sectional shape as will be apparent to those skilled in the art.

Each bracket 13 preferably consists of a body having a substantially flat first face 19, a substantially flat second face 21, and four substantially flat side walls 23 joining the first and second faces 19, 21 (see, in general, FIGS. 3-8). A slot 25 is preferably provided in the first face 19 of each bracket 13 for receiving the arch wire 17. Each bracket 13 may also include at least one and preferably a spaced-apart pair of grooves 27 in the first face 19 thereof and extending partway thereacross and at least one and preferably a pair of spaced-apart grooves 29 in the second face 21 thereof for reasons which will hereinafter become apparent. The grooves 27, 29 preferably extend transverse to the slot 25. An aperture 31 may also be provided in each bracket 13 for reasons which will hereinafter become apparent. The specific construction, size and material of each bracket 13 may vary as will be apparent to those skilled in the art. For example, each bracket 13 may be machined out of metal or the like.

Figure 2:
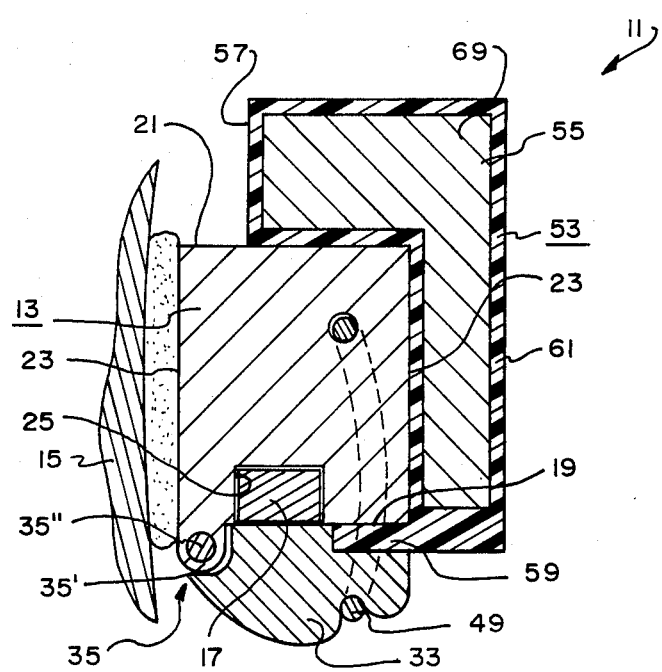
FIG. 2 is a sectional view substantially as taken on line II—II of FIG. 1.
Figure 3:
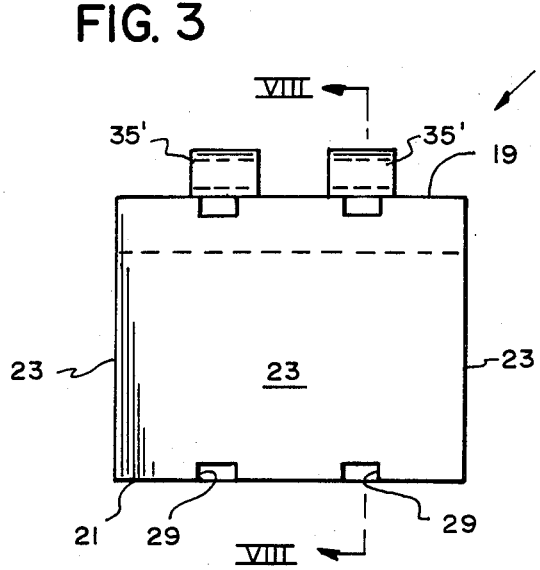
FIGS. 3-7 are orthographic views of a bracket of the orthodontic appliance of the present invention.
Figure 4:
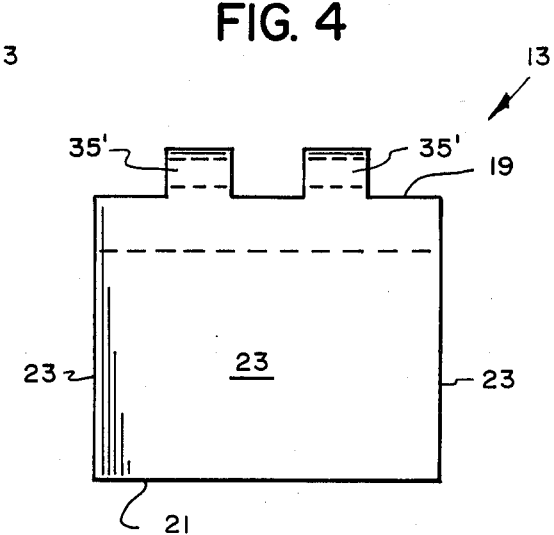
Figure 5:
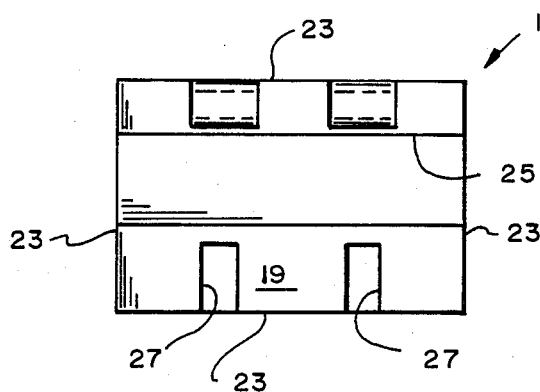
Figure 6:
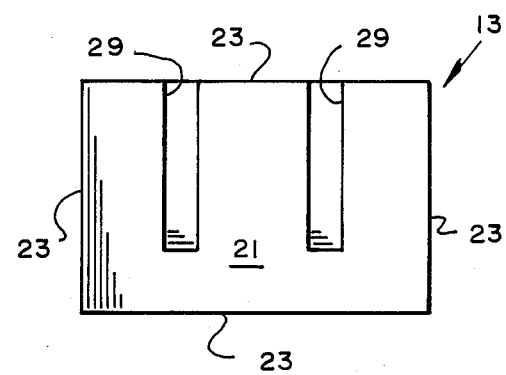
Figure 7:
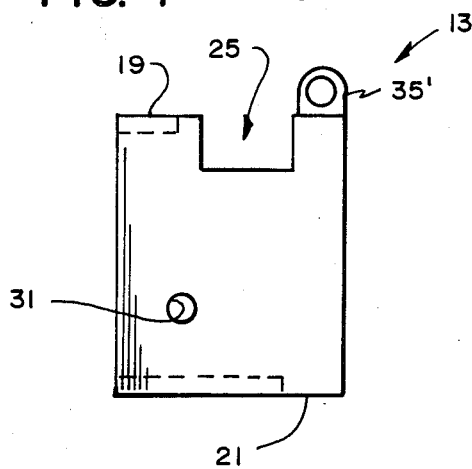
Figure 8:
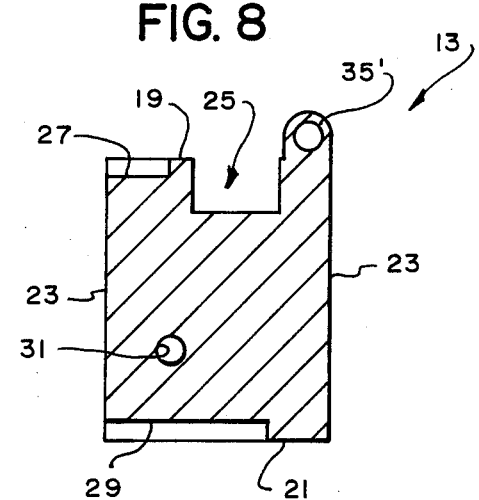
FIG. 8 is a sectional view substantially as taken on line VIII—VIII of FIG. 3.
Figure 20:
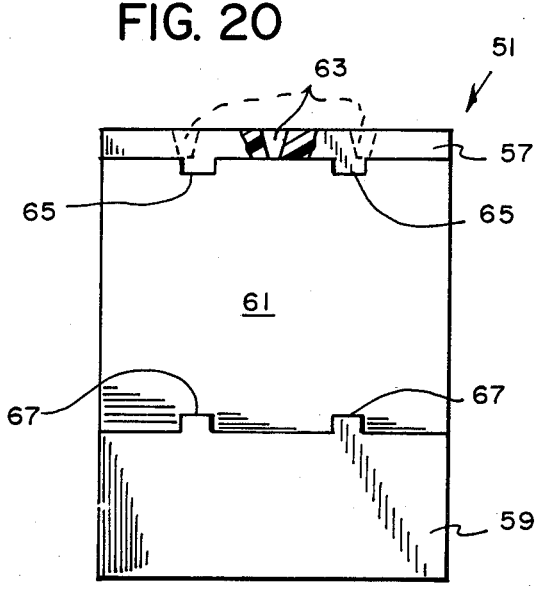
Figure 21:
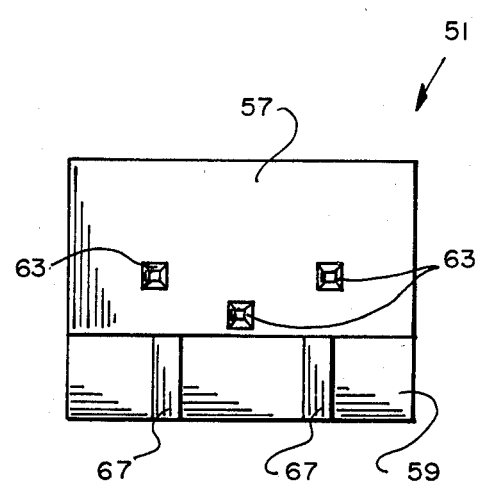
Figure 22:
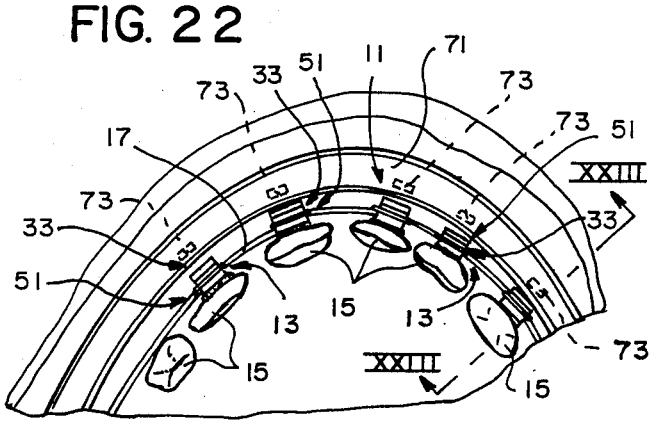
FIG. 22 is a somewhat diagrammatic view of a patient's mouth showing the orthodontic appliance of the present invention in use.
Figure 23:
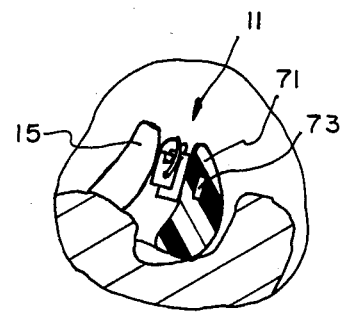
FIG. 23 is a sectional view substantially as taken on line XXIII—XXIII of FIG. 22.

The appliance 11 includes a cap 33 for each bracket 13 (see, in general, FIGS. 9-14). Each cap 33 is adapted to fit over the first face 19 of a bracket 13 to thereof trap the arch wire 17 within the slot 25 as shown in FIGS. 1 and 2. A hinge means 35 may be provided for pivotally attaching each cap 33 to a bracket 13 for movement between an opened position in which the arch wire 17 can be placed in or removed from the slot 25 in the bracket 13, as shown in FIG. 16, and a closed position in which the arch wire 17 is held within the slot 25 (see FIGS. 1, 2 and 17). Each cap 33 has a first face 37, a second face 39 with the hinge means 35 mounted substantially between the first face 37 of the cap 33 and the first face 19 of the bracket 13 whereby the first faces 37, 19 will substantially contact one another when the cap 33 is in the closed position. Each cap 33 preferably has three outwardly directed post members 41 extending from the first face 37 thereof and a groove 43 in the second face 39 thereof for reasons which will hereinafter become apparent. Two of the post members 41 are preferably staggered relative to the other post member 41, as clearly shown in FIGS. 12 and 13 for reasons which will hereinafter become apparent. The post members 41 are preferably tapered as clearly shown in FIGS. 9 and 13. The groove 43 preferably extends substantially parallel with the slot 25 in the bracket 13. At least one corner or edge of the cap 33 is preferably somewhat rounded as at 45 (see FIGS. 13 and 14) substantially adjacent the second face 39 and groove 43 thereof for reasons which will hereinafter become apparent. The first face 37 of each cap 33 is preferably provided with an offset portion 47 whereby a space is provided between the first space 37 of the cap 33 and the first space 19 of the bracket 13 adjacent the post members 41 in the cap 33 and the groove 27 in the first face 19 of the bracket 13 (see FIG. 17) for reasons which will hereinafter become apparent. The specific construction, size and material of the cap 33 and hinge means 35 may vary as will be apparent to those skilled in the art. Thus, the cap 33 may be machined out of metal and the hinge means 35 may consist simply of a plurality of ears 35' attached respectively to the bracket 13 and cap 33, and a pivot rod 35" coupling the various ears to one another.

The appliance 11 includes a clamp means for holding the cap 33 against the face 19 of the bracket 13. The clamp means may included a bail member 49 attached to each bracket 13 and extending over the cap 33 associated with that bracket 13 to hold the cap 33 to the bracket 13 and to coact with the cap 33 to hold the arch wire 17 within the slots 25 (see FIGS. 1, 2, 15, 16 and 17). The bail member 49 is preferably pivotally attached to the respective bracket 13 for movement between a first position in which the cap 33 is allowed to pivot between the opened and closed positions (see FIG. 16) and a second position in which the cap is held in the closed position (see FIGS. 1, 2 and 17). The bail member 49 may consist simply of a wire loop, as shown in FIG. 15, having a first portion extending through the aperture 31 in the respective bracket 13 and having a second portion for being selectively positioned over the rounded edge 45 of the cap 33 when the cap 33 is in the closed position and for engaging the groove 43 in the second face 39 of the cap 33 to thereby hold the cap 33 in the closed position. The bail member 49 preferably has spring-like properties whereby it may be manually urged between the first and second positions over the rounded edge or corner 45 of the cap 33 in a manner which will now be apparent to those skilled in the at. The specific construction, material and size of the bail member 49 may vary as will now be apparent to those skilled in the art. Thus, for example, the bail member 49 may be bent from metal wire or the like.

The appliance 11 may include an auxiliary means 51 attached to one or more brackets 13 for exerting additional corrective force against the patient's teeth through the bracket 13 (see FIGS. 1, 2, 18–21). Each auxiliary means 51 includes an auxiliary body member 53 for being securely attached to a bracket 13 and includes a force means 55 attached to the auxiliary body member 53 for exerting additional corrective force against the patient's teeth 15. The auxiliary body member 53 may consist substantially of a channel-shaped member having a first flange 57 for engaging the first face 19 of the bracket 13, a second flange 59 for engaging the second face 21 of the bracket 13, and a bridge 61 joining the first and second flanges 57, 59 to one another. The first flange 57 is preferably shaped in size so as to extend into the offset portion 47 of the cap 33 when the cap 33 is in the closed position (see FIG. 2) whereby the first flange 57 will be fixedly secured to the bracket 13 when the cap 33 is in the closed position and the bail member 49 is in the second position. The first flange 57 of the auxiliary body member 53 preferably has three cavities 63 therein shaped and spaced so as to receive the post members 41 of the cap 33 when the cap 33 is in the closed position and the auxiliary body member 53 is attached to the bracket 13. The auxiliary body member 53 also may have at least one and preferably a spaced-apart pair of inwardly directed ridges 65 on the first flange 59 thereof for being received in the groove 27 in the first face 19 of the bracket 13 when the auxiliary body member 53 is attached to the bracket 13. Additionally, the auxiliary body member 53 may include at least one and preferably a pair of inwardly directed ridges 67 on the second flange 59 thereof for being received in the grooves 29 in the second face 21 of the bracket 13 when the auxiliary body member 53 is attached to the bracket 13. Thus, the cavities 63 and the ridges 65, 67 are positioned and sized so as to coact with the respective post members 41 and grooves 27, 29 when the auxiliary body member 53 is attached to the bracket 13 and the cap 33 is in the closed position to properly position and securely hold the auxiliary body member 53 to the bracket 13. This arrangement of grooves and ridges allows the auxiliary body member 53 to be easily slid onto the bracket 13 when the cap 33 is in the opened position and causes the auxiliary body member 53 to be securely attached to the bracket 13 when the cap 33 is in the closed position and the bail member 49 is in the second position. The specific construction, material and size of the auxiliary body member 53 may vary as will now be apparent to those skilled in the art. Thus, for example, the auxiliary body member 53 may be molded or otherwise formed out of plastic or the like.

The force means 55 may include a magnet 69 for being attached to the auxiliary body member 53 and for exerting additional corrective force against the patient's teeth 15 in a manner which will be apparent to those skilled in the art. Thus, for example, the magnetic poles of the magnet 69 of one auxiliary means 51 attached to one bracket 13 may be positioned so as to be drawn toward an adjacent auxiliary means 51 of an adjacent bracket 13 to thereby draw the adjacent teeth 15 toward one another. The magnet 69 is preferably completely covered or encased within the auxiliary body member 53. It should be noted that the force means 55 may consist of other well-known structure for applying additional force to the patient's teeth. Thus, for example, the force means 55 may include a hook means or the like (not shown) attached to the auxiliary body member 53 for coacting with a plastic ringlet or the like extending from adjacent hook means as will be apparent to those skilled in the art.

The appliance 11 may include bumper means 71 for fitting over the brackets 13, caps 33, bail members 49 and auxiliary means 51. Magnets 73 may be molded within or otherwise attached to the bumper means 71 to interact with the magnets 69 to create a force between the bumper means 71 and the auxiliary body members 53 for causing the desired tooth movement.

To use the appliance 11 the brackets 13 are attached to specific teeth 15 in any typical manner, such as by way of adhesives, and on either the labial, buccal or lingual side, etc. The placement and location of the brackets 13 will be determined in the ordinary manner. Next, the arch wire 17 is attached to the brackets 13 by moving the cap 33 to the opened position to allow the arch wire 17 to be inserted into the slot 25 and then moving the cap 33 to the closed position and moving the bail member 49 to the second position to thereby lock the arch wire 17 to the brackets 13. The various bends and the like in the arch wire 17 or angulations of slot 25 in bracket 13 for exerting corrective force through the brackets 13 will be determined in the ordinary manner. If additional force is desired, the auxiliary means 51 can be attached to the brackets 13 by sliding the auxiliary body member 53 onto the brackets 13 when the cap 33 is in the open position. The specific type of and direction of force to be applied by the auxiliary means 51 is selected in any manner now apparent to those skilled in the art.

As thus constructed and used, the present invention provides self-locking brackets which need no ligature ligation, which permits tension setting of the arch wire in the arch wire slot of the bracket, which permits other alteration attachments to be used in place of the magnets 69 without bracket or band removal, which can apply force in all planes of space. Thus, for example, the magnets 69 could be replaced by typical hooks, elastic band members, tubes, uprighting springs, etc., which can be clamped between a bracket 13 and cap 33 or attached directly to the bridge 61 of the body member 53, etc.

Although the present invention has been described and illustrated with respect to a preferred embodiment thereof and a preferred use therefor, it is not to be so limited since changes and modifications can be made therein which are within the full intended scope of the invention.

I claim:

1. An orthodontic appliance of the type including an arch wire for causing a corrective force to be exerted against a patient's teeth, wherein said improvement comprises:
   (a) a bracket for being fixedly attached to one of the patient's teeth, said bracket having a face surface and having a slot in said face surface for receiving said arch wire;
   (b) a cap provided over said face surface of said bracket;
   (c) hinge means for pivotally attaching said cap to said bracket for movement between an opened position in which said arch wire can be placed in or removed from said slot in said bracket and a closed position in which said arch wire is held within said slot;
   (d) clamp means for holding said cap against said face surface of said bracket to coact with said cap to hold said arch wire within said slot, said clamp means including a bail member attached to said bracket and extending over said cap, said bail member being pivotally attached to said bracket for movement between a first position in which said cap is allowed to pivot between said open and closed positions and a second position in which said cap is held in said closed position; and
   (e) an auxiliary means attached to said bracket for exerting additional corrective force against the patient's teeth through said bracket, said auxiliary means including an auxiliary body member for being securely attached to said bracket and including a force means attached to said auxiliary body member for exerting additional corrective force against the patient's teeth; said auxiliary body member including a first flange for engaging said face surface of said bracket, including a second flange for engaging the surface of said bracket opposite said face surface thereof, and including a bridge joining said first and second flanges thereof; said first flange being fixedly secured to said bracket when said cap is in said closed position and said bail member is in said second position.

2. The appliance of claim 1 in which said cap has an offset portion for receiving a portion of said first flange of said auxiliary body member when said cap is in said closed position.

3. The appliance of claim 2 in which said cap has a plurality of outwardly directed post members, and in which said first flange of said auxiliary body member has a plurality of cavities for receiving said post members of cap when said auxiliary body member is attached to said bracket and said cap is in said closed position.

4. The appliance of claim 3 in which said second flange of said auxiliary body member has at least one inwardly directed ridge, and in which said bracket has at least one groove for receiving said at least one inwardly directed ridge of said second flange of said auxiliary body member when said auxiliary body member is attached to said bracket.

5. The appliance of claim 4 in which said first flange of said auxiliary body member has at least one inwardly directed ridge, and in which said bracket has at least one groove for receiving said at least one inwardly directed ridge of said first flange of said auxiliary body member when said auxiliary body member is attached to said bracket.

6. The appliance of claim 1 in which said force means includes a magnet for being attached to said auxiliary body member and for exerting additional corrective force against the patient's teeth.

7. The appliance of claim 6 in which said auxiliary body member is formed out of plastic and in which said magnet is completely covered by said plastic.

8. The appliance of claim 6 in which is included a plurality of said brackets, said caps, said bail members and said auxiliary means.

9. The appliance of claim 8 in which is included bumper means for fitting over said brackets, said caps, said bail members and said auxiliary means, and in which is included a plurality of magnets attached to said bumper means for interacting with said magnets of said auxiliary means.

* * * * *